United States Patent
Katrana et al.

(10) Patent No.: US 8,246,687 B2
(45) Date of Patent: Aug. 21, 2012

(54) SHOULDER PROSTHETIC

(75) Inventors: Nicholas J. Katrana, Ft. Wayne, IN (US); Nathan A. Winslow, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 161 days.

(21) Appl. No.: 12/620,834

(22) Filed: Nov. 18, 2009

(65) Prior Publication Data

US 2011/0118846 A1 May 19, 2011

(51) Int. Cl.
*A61F 2/40* (2006.01)

(52) U.S. Cl. .................................................. 623/19.13

(58) Field of Classification Search ...... 623/19.11–19.14
See application file for complete search history.

(56) References Cited

U.S. PATENT DOCUMENTS

| | | |
|---|---|---|
| 3,979,778 A | 9/1976 | Stroot |
| 4,024,588 A | 5/1977 | Janssen et al. |
| 4,042,980 A | 8/1977 | Swanson et al. |
| 4,261,062 A | 4/1981 | Amstutz et al. |
| 4,328,593 A | 5/1982 | Sutter et al. |
| 4,470,158 A | 9/1984 | Pappas et al. |
| 4,550,450 A | 11/1985 | Kinnett |
| 4,919,670 A | 4/1990 | Dale et al. |
| 5,314,479 A | 5/1994 | Rockwood, Jr. et al. |
| 5,314,492 A | 5/1994 | Hamilton et al. |
| 5,358,526 A | 10/1994 | Tornier |
| 5,549,682 A | 8/1996 | Roy |
| 5,910,171 A | 6/1999 | Kummer et al. |
| 5,957,979 A * | 9/1999 | Beckman et al. .......... 623/20.33 |
| 5,989,293 A | 11/1999 | Cook et al. |
| 6,045,582 A | 4/2000 | Prybyla |
| 6,120,542 A | 9/2000 | Camino et al. |
| 6,129,764 A | 10/2000 | Servidio |
| 6,197,062 B1 | 3/2001 | Fenlin |
| 6,197,063 B1 | 3/2001 | Dews et al. |
| 6,589,282 B2 | 7/2003 | Pearl |
| 6,620,197 B2 | 9/2003 | Maroney et al. |
| 6,673,114 B2 | 1/2004 | Hartdegen et al. |
| 6,783,549 B1 | 8/2004 | Stone et al. |

(Continued)

FOREIGN PATENT DOCUMENTS

DE 4220217 A1 12/1993

(Continued)

OTHER PUBLICATIONS

International Search Report and Written Opinion for European Patent Application No. 10191566.8 dated Mar. 21, 2011.

(Continued)

*Primary Examiner* — Bruce E Snow
(74) *Attorney, Agent, or Firm* — Harness, Dickey (57) ABSTRACT

A shoulder implant assembly including a humeral stem, a head, a cup, and a taper adaptor. The humeral stem is configured to be inserted into a humerus bone. The head includes a metal substrate having a coupling taper and a polymeric cover mounted to the metal substrate having a convex outer surface and a generally planar base. The cup has a concave surface configured to articulate with the polymeric cover of the head. The taper adaptor is configured to mate with the coupling taper of the head. The taper adaptor is configured to connect the head to the stem when the cup is connected to a glenoid. The taper adaptor is configured to connect the head to the glenoid when the cup is connected to the humeral stem.

8 Claims, 11 Drawing Sheets

U.S. PATENT DOCUMENTS

| | | |
|---|---|---|
| 6,800,095 B1 | 10/2004 | Pope et al. |
| 6,875,238 B1 * | 4/2005 | Price .................... 623/23.11 |
| 7,431,874 B2 | 10/2008 | Muratoglu et al. |
| 7,498,365 B2 | 3/2009 | Muratoglu et al. |
| 7,790,095 B2 | 9/2010 | Muratoglu et al. |
| 7,906,064 B2 | 3/2011 | Muratoglu et al. |
| 2001/0047210 A1 | 11/2001 | Wolf |
| 2002/0022889 A1 | 2/2002 | Chibrac et al. |
| 2002/0099381 A1 | 7/2002 | Maroney |
| 2002/0099445 A1 | 7/2002 | Maroney et al. |
| 2003/0028253 A1 | 2/2003 | Stone et al. |
| 2003/0144738 A1 | 7/2003 | Rogalski |
| 2004/0002765 A1 | 1/2004 | Maroney et al. |
| 2004/0034431 A1 | 2/2004 | Maroney et al. |
| 2004/0193277 A1 | 9/2004 | Long et al. |
| 2004/0193278 A1 | 9/2004 | Maroney et al. |
| 2005/0021038 A1 | 1/2005 | Maroney |
| 2005/0065612 A1 | 3/2005 | Winslow |
| 2005/0194723 A1 | 9/2005 | Muratoglu et al. |
| 2005/0197708 A1 * | 9/2005 | Stone et al. ................ 623/19.12 |
| 2006/0036328 A1 | 2/2006 | Parrott et al. |
| 2006/0116774 A1 | 6/2006 | Jones et al. |
| 2007/0198094 A1 | 8/2007 | Berelsman et al. |
| 2008/0109081 A1 * | 5/2008 | Bao et al. .................. 623/17.15 |
| 2008/0215156 A1 | 9/2008 | Duggal et al. |
| 2009/0118837 A1 | 5/2009 | Winslow et al. |
| 2009/0192621 A1 | 7/2009 | Winslow et al. |
| 2009/0265001 A1 | 10/2009 | Muratoglu et al. |

FOREIGN PATENT DOCUMENTS

| | | |
|---|---|---|
| EP | 0617934 | 10/1994 |
| EP | 0845250 | 6/1998 |
| EP | 1064890 | 1/2001 |
| EP | 1464305 | 10/2004 |
| EP | 1782765 A1 | 5/2007 |
| FR | 2578739 A1 | 9/1986 |
| FR | 2880793 | 7/2006 |

OTHER PUBLICATIONS

Two engineering drawings illustrating a humeral head replacement device.

Copeland Humeral Resurfacing Head, Biomet Orthopedics, Inc., copyright 2001.

Global Advantange CTA Humeral Head, Dupuy Orthopaedics, copyright 2000.

European Search Report and Written Opinion for EP04255049 mailed Nov. 17, 2005.

Wang, A. et al., Carbon Fiber Reinforced Polyether Ether Ketone Composite as a Bearing Surface for Total Hip Replacement, Tribology International vol. 31, No. 11, pp. 661-667 (1998).

Howling, G.I. et al., Biological Response to Wear Debris Generated in Carbon Based Composites as Potential Bearing Surfaces for Artificial Hip Joints, Wiley Periodicals, Inc., pp. 758-764 (2003).

* cited by examiner

SHOULDER PROSTHETIC

FIELD

The present disclosure relates to an implant for shoulder joint replacement.

BACKGROUND

This section provides background information related to the present disclosure which is not necessarily prior art.

A natural shoulder joint may undergo degenerative changes for a variety of different reasons. When these degenerative changes become advanced and irreversible, it may become necessary to replace a natural shoulder joint with a prosthetic shoulder joint.

Shoulder joint implants often include a humeral component and a glenoid component. The humeral component generally includes a stem, a head, and an adaptor for coupling the head with the stem. The head is often made of metal, such as cobalt-chrome. The glenoid component is generally modular and includes a metal tray and a bearing mounted thereto. The bearing includes an articulating surface that receives and articulates with the head. The bearing is often made out of an ultra-high molecular weight polyethylene ("UHMWPE") material.

While such shoulder implants are suitable for their intended use, it would be desirable to provide a shoulder implant having a reduced weight to decrease the amount of stress that is typically transferred through the implant to the bone and/or soft tissue. Further, it would be desirable to provide a shoulder implant that permits less bone to be resected during implantation, reduces wear between the components, enhances fixation of the glenoid component, and facilitates postoperative procedures.

SUMMARY

This section provides a general summary of the disclosure, and is not a comprehensive disclosure of its full scope or all of its features.

The present teachings provide for a shoulder implant assembly including a humeral stem, a head, a cup, and a taper adaptor. The humeral stem is configured to be inserted into a humerus bone. The head includes a metal substrate having a coupling taper and a polymeric cover mounted to the metal substrate having a convex outer surface and a generally planar base. The cup has a concave surface configured to articulate with the polymeric cover of the head. The taper adaptor is configured to mate with the coupling taper of the head. The taper adaptor is configured to connect the head to the stem when the cup is connected to a glenoid. The taper adaptor is configured to connect the head to the glenoid when the cup is connected to the humeral stem.

The present teachings further provide for a shoulder implant assembly including a humeral stem, a polymeric head, a cup, and a taper adaptor. The humeral stem is configured to be inserted into a humerus bone. The polymeric head includes a convex outer surface, a polymeric coupling taper, and a generally planar base. The cup has a concave surface configured to articulate with the polymeric head. The taper adaptor is configured to mate with the polymeric coupling taper of the head. The taper adaptor is configured to connect the head to the stem when the cup is connected to a glenoid. The taper adaptor is configured to connect the head to the glenoid when the cup is connected to the humeral stem.

The present teachings also provide for a head for a shoulder implant assembly that includes a polymeric cover and a metal substrate. The polymeric cover includes a convex outer surface and a generally planar base. The metal substrate has the polymeric cover mounted thereto. The metal substrate includes a coupling taper, a retention flange to secure the polymeric cover to the metal substrate, and an anti-rotation tab to prevent the polymeric cover from rotating about the metal substrate.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Figure 1:
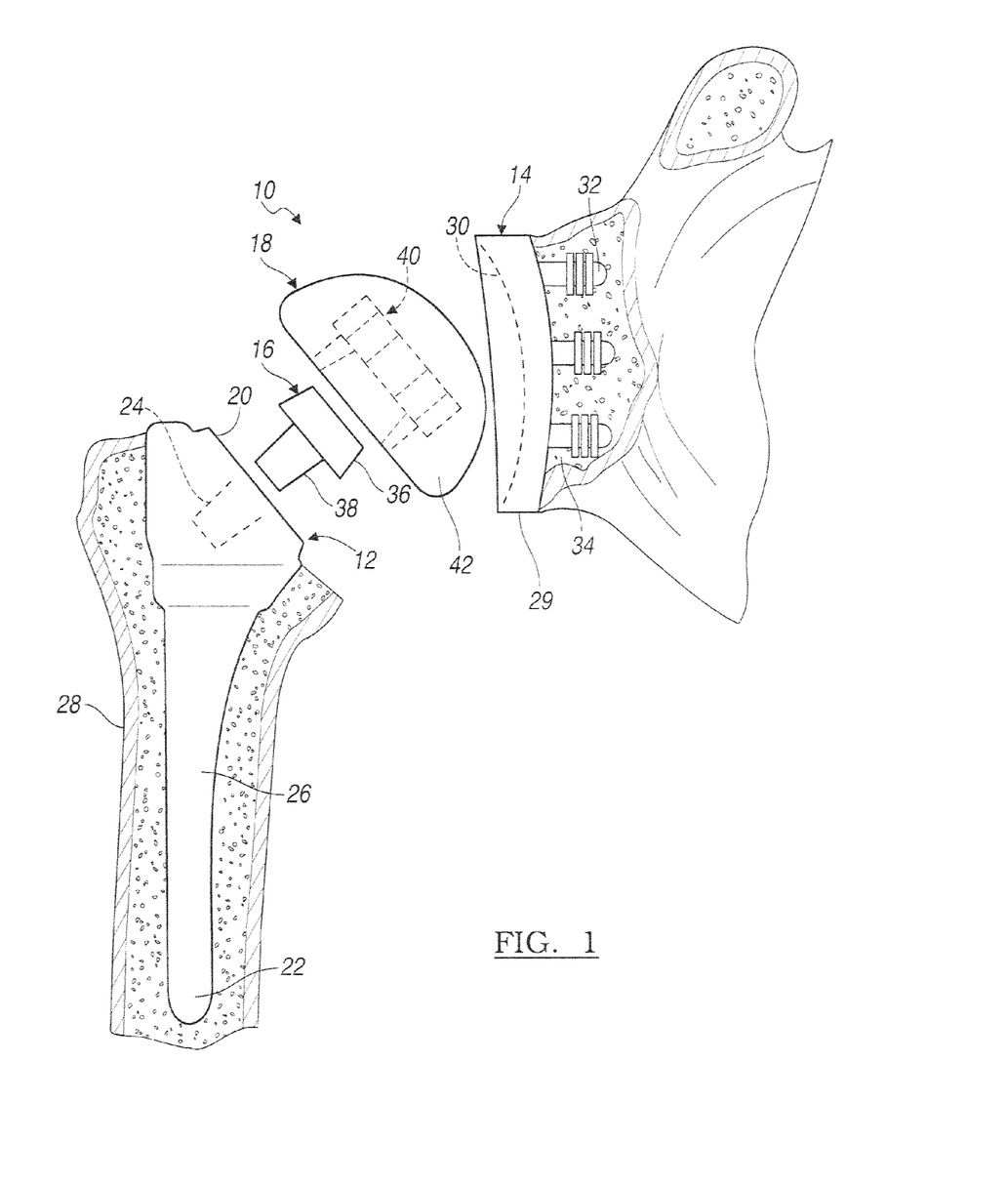
FIG. 1 is an exploded view of a shoulder implant assembly in accordance with various embodiments of the present teachings.

With initial reference to FIG. 1, a shoulder implant assembly according to various embodiments of the present teachings is illustrated at reference numeral 10. While the present invention is described herein with reference to a shoulder implant assembly, one skilled in the art will recognize that the invention is equally applicable to a variety of other implants as well, such as any suitable implant configured to replace what is commonly referred to in the art as a ball-in-socket joint, including a hip replacement implant.

The implant assembly 10 generally includes a humeral stem 12, a cup 14, a taper adaptor 16, and a head 18.

The humeral stem 12 includes a proximal end 20 and a distal end 22. The proximal end 20 includes a female taper 24 configured to receive the taper adaptor 16. The distal end 22 is at the end of an elongated portion 26 that is configured to be received in a humerus bone 28. The humeral stem 12 can be made of any suitable biocompatible material, such as cobalt-chrome and/or titanium.

Figure 2A:
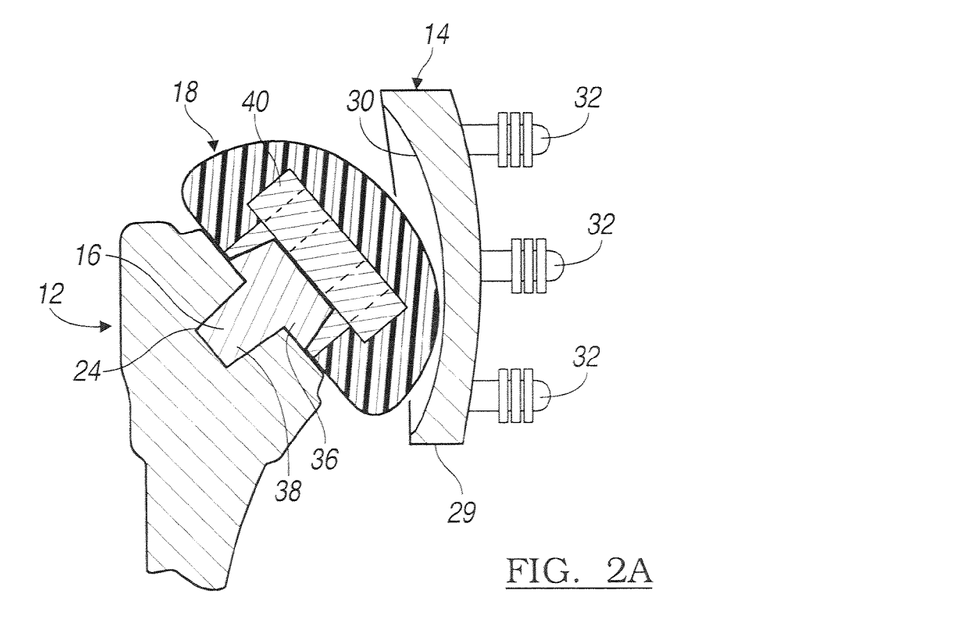
FIG. 2A is a cross-sectional view of the implant assembly of FIG. 1 illustrating the interaction between different components of the assembly.
Figure 2B:
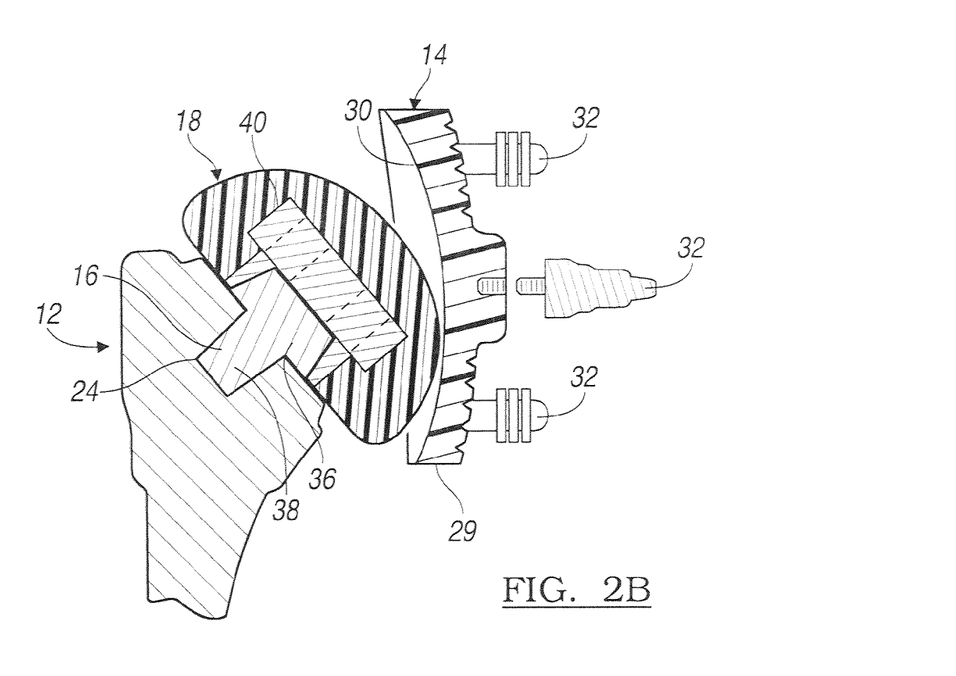
FIG. 2B is a cross-sectional view of an implant assembly according to another aspect of the present teachings.

With additional reference to FIGS. 2A and 2B, the cup 14 includes a unitary base 29 having a convex articulating surface 30 formed therein. Extending from a side of the base 24 that is opposite to the convex articulating surface 30 are one or more mounting posts 32. The mounting posts 32 can take the form of any suitable mounting or connecting device, such as a fixation peg or screw, suitable to secure the cup 14 to a glenoid cavity 34. The mounting posts 32 can be unitary with the base 29 or modular. The cup 14 can be made of any suitable material, including metals (FIG. 2A) and polymers (FIG. 2B). Suitable metals include cobalt chrome and/or titanium. Suitable polymers include ultra-high molecular weight polyethylene, polyether ether ketone ("PEEK"), carbon fiber reinforced PEEK (such as PEEK-OPTIMA® from Invibio, Ltd. of the United Kingdom), and/or vitamin E stabilized highly crosslinked polyethylene (HXLPE), such as is disclosed in U.S. Pat. No. 7,431,874. U.S. Pat. No. 7,431,874 is incorporated by reference herein, as well as are all patent applications and issued patents that rely thereon for priority including the following U.S. patent application Ser. No. 11/104,580 filed on Apr. 13, 2005; U.S. patent application Ser. No. 11/104,582 filed on Apr. 13, 2005; U.S. patent application Ser. No. 11/564,594 filed on Nov. 29, 2006; U.S. patent application Ser. No. 11/948,393 filed on Nov. 30, 2007; and U.S. patent application Ser. No. 12/464,235 filed on May 12, 2009. An exemplary vitamin E stabilized HXLPE that may be used includes E1™ Antioxidant Infused Technology offered by Biomet Orthopedics, Inc. of Warsaw, Ind.

The taper adaptor 16 generally includes a first male taper 36 and a second male taper 38. The first and the second male tapers 36 and 38 are each generally cylindrical. The first male taper 36 has a larger diameter than the second male taper 38. The first male taper 36 is angled to cooperate with a corresponding taper of the head 18, as further described herein. The second male taper 38 is angled to cooperate with the female taper 24 of the humeral stem 12 to create a Morse taper lock between the taper adaptor 16 and the humeral stem 12. The taper adaptor 16 can be made of any suitable material, such as cobalt chrome and/or titanium.

Figure 3A:
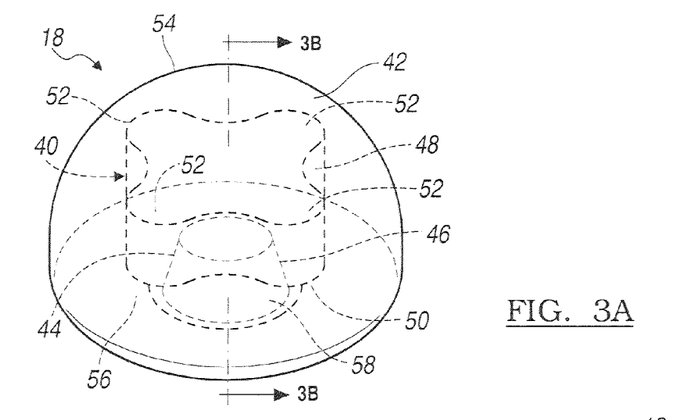
FIG. 3A is a perspective view of a head of the implant assembly of FIG. 1.
Figure 3B:
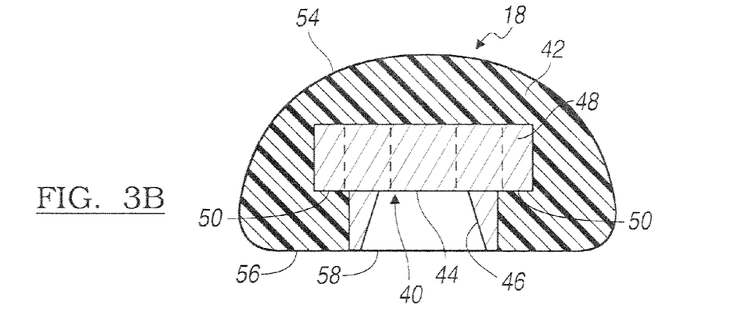
FIG. 3B is a cross-sectional view of FIG. 3A taken along line 3B-3B of FIG. 3A.
Figure 3C:
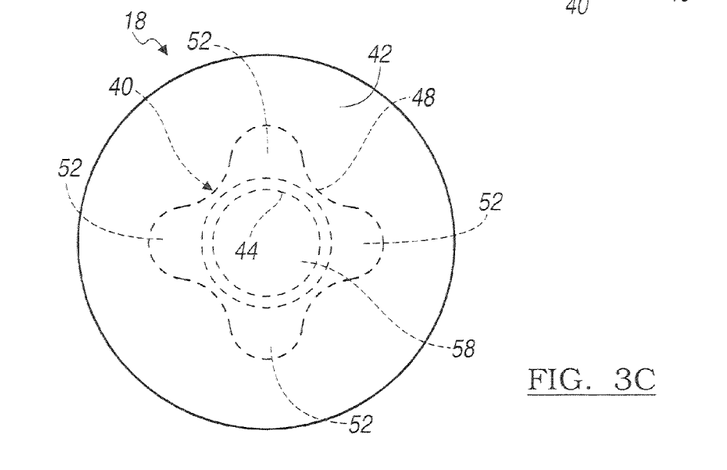
FIG. 3C is a top view of the head of FIG. 3A.

With additional reference to FIGS. 3A-3C, the head 18 generally includes a metallic substrate 40 and a polymeric cover 42. The metallic substrate 40 can be made from any suitable metal, including cobalt-chrome and/or titanium. The metallic substrate 40 includes a coupling taper 44 having angled sidewalls 46. The sidewalls 46 are angled to receive the first male taper 36 of the taper adaptor 16 to connect the head 18 to the taper adaptor 16 with a Morse taper. The sidewalls 46 extend from a base 48 of the metallic substrate 40.

The base 48 generally includes a retention feature to secure the polymeric cover 42 to the substrate 40 and an anti-rotation feature to prevent the cover 42 from rotating about the substrate 40. As illustrated, the retention feature includes a flange 50 and the anti-rotation feature includes tabs 52. The base 48 is illustrated to include four tabs 52, but any suitable number of tabs can be provided, as well as any irregular, non-circular surface.

The polymeric cover 42 includes a concave outer surface 54, a generally planar base surface 56, and a generally circular opening 58 defined by the base surface 56. The polymeric cover 42 sits atop the base 48 of the metallic substrate 40 and extends around the flange 50 of the base 48. The flange 50 prevents the polymeric cover 42 from separating from the substrate 40. The tabs 52 prevent the polymeric cover 42 from rotating about the substrate 40.

The polymeric cover 42 can be made of any suitable biocompatible material, such as polyether ether ketone ("PEEK") and/or carbon fiber reinforced PEEK. For example, carbon fiber reinforced PEEK-OPTIMA® from Invibio, Ltd. of the United Kingdom can be used. The polymeric cover 42 can also include vitamin E stabilized (HXLPE). An exemplary vitamin E stabilized HXLPE that may be used includes E1™ Antioxidant Infused Technology offered by Biomet Orthopedics, Inc. of Warsaw, Ind.

The polymeric cover 42 can be mounted to the substrate 40 in any suitable matter. For example, the polymeric cover 42 can be injection molded over the substrate 40 such that the cover 42 extends around the flange 50. The polymeric cover 42 and the substrate 40 can be finished before or after the molding process. For example, the polymeric cover 42 without the concave outer surface 54 can be molded over the substrate 40 with the coupling taper 44 not yet formed therein. The coupling taper 44 can subsequently be machined in the substrate 40 and the concave outer surface 54 can be machined in the cover 42. To machine the coupling taper 44, the head 18 can be supported by the unmachined cover 42, which is often in the form of a blank block of PEEK or HXLPE for example, or support features provided in unmachined cover 42, such as chucking stubs. To machine the concave outer surface 54, the head 18 can be supported at the coupling taper 44. The concave outer surface 54 is shaped to permit articulation with the convex articulating surface of the cup 14.

The height of the head 18 can be customized as necessary for different patients. For example, if a lower, or flatter, head is desirable, less polymeric material can be used over the substrate 40 and/or the base 48 of the substrate 40 can be made thinner. Conversely, if a higher or more rounded head is desirable, additional polymeric material can be used over the substrate 40 and/or the base 48 can be made thicker.

Thus, with renewed reference to FIG. 1, the implant assembly 10 is operable to replace an anatomical shoulder joint. The polymeric cover 42 provides the head 18 with a reduced weight as compared to heads that are entirely made of metal. The reduced weight decreases the amount of stress that is typically transferred through the implant to the surrounding bones and/or soft tissue. Further, the metallic cup 14 of FIG. 2A can be made generally thinner than a modular polymeric cup, thereby reducing the amount of bone that is typically resected at the glenoid cavity 34. This allows more bone stock to be retained to enhance fixation and facilitate post-operative revision surgery. Also, with a metallic cup 14, the surface area of the cup 14 can be provided with an increased porous portion to enhance bone in-growth.

Figure 4:
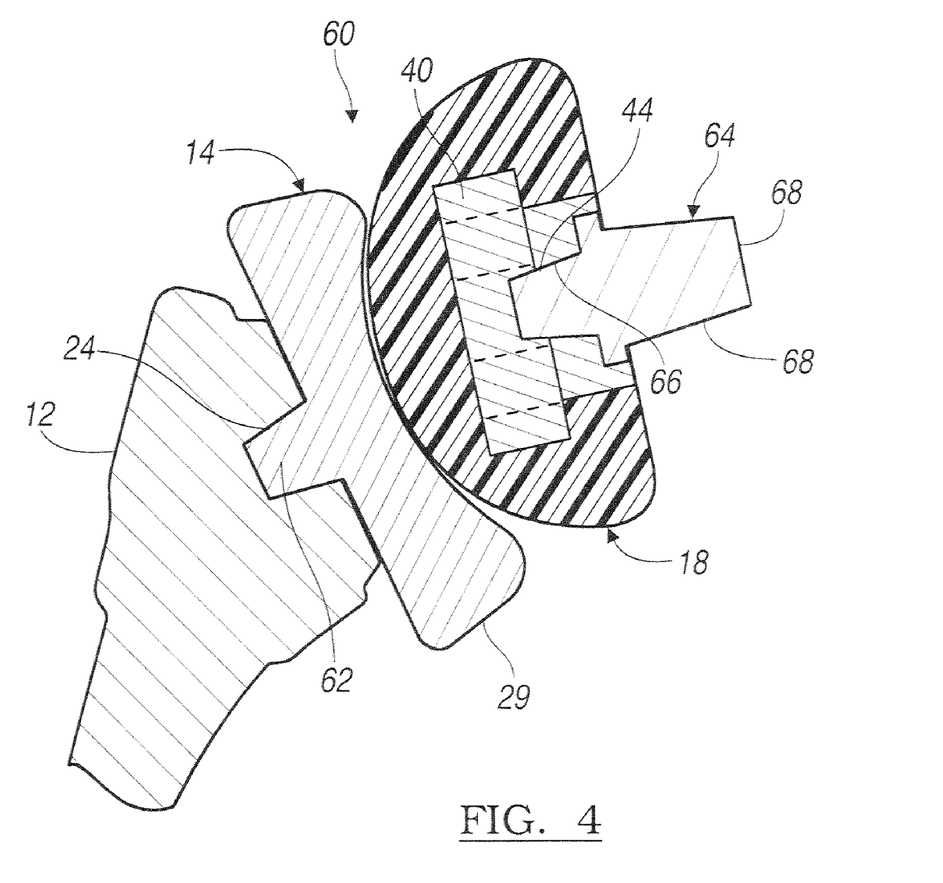
FIG. 4 is a cross-sectional view of an implant assembly according to a further aspect of the present teachings.

One skilled in the art will recognize that providing the head 18 with a polymeric cover 42 is applicable to a variety of other applications, as is the metallic cup 14. For example and with additional reference to FIG. 4, the head 18 can be used in a reverse shoulder implant assembly 60. With the reverse shoulder implant assembly 60, the cup 14 is mounted to the humeral stem 12 with a taper connection between a male taper 62 of the cup 14 and the female taper 24 of the humeral stem 12. The head 18 is mounted in the glenoid cavity 34 (illustrated in FIG. 1) with a mounting stem 64. The mounting stem 64 includes a male taper 66 that is sized to mate with the coupling taper 44 of the head 18 and an elongated portion 68 that can be implanted directly in the glenoid cavity 34 or mounted to an intermediate mounting device that is mounted in the glenoid cavity 34.

Figure 5A:
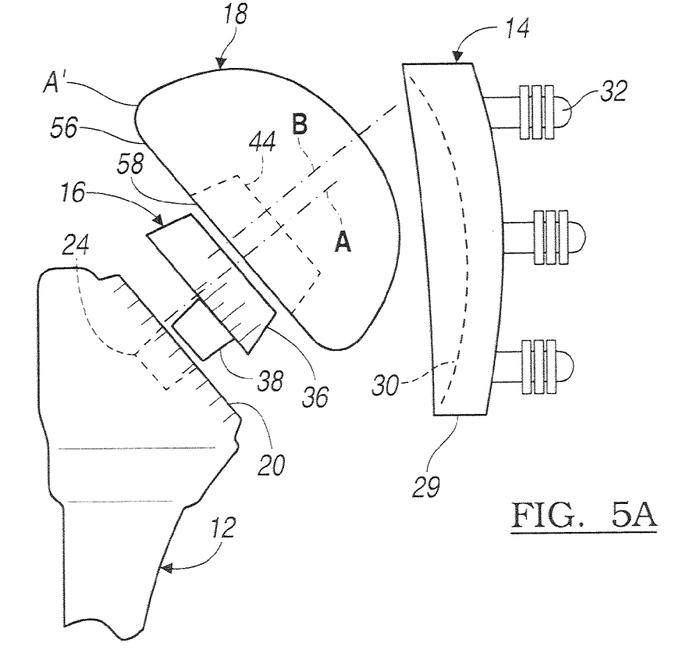
FIG. 5A is a side view of an offset implant assembly according to the present teachings with a head of the assembly at a first position.
Figure 5B:
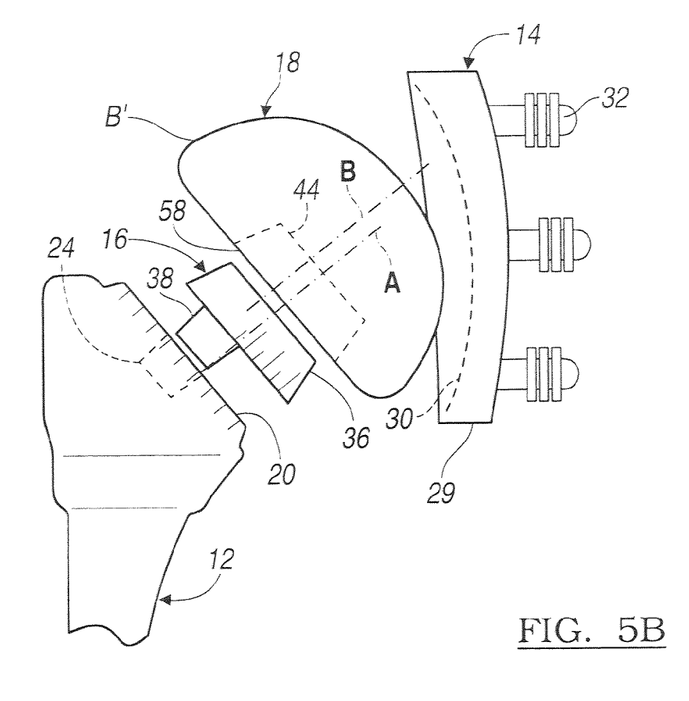
FIG. 5B is a side view of the implant assembly of FIG. 5A with the head at a second position.

With additional reference to FIGS. 5A and 5B, the head 18 can also be offset in order to provide for a more accurate reproduction of the natural anatomy. When the head 18 is offset, an axis A of the circular opening 58 in the base 48, as well as the coupling taper 44, is offset from an axis B of the polymeric cover 42 and the overall head 18. Further, the first male taper 36 of the taper adaptor 16 can be offset from the second male taper 38. By rotating the taper adaptor 16 and/or the head 18, the head 18 can be moved to a desired offset position, such as from position A' (FIG. 5A) to offset position B' (FIG. 5B), as is provided for in the Versa-Dial® glenosphere and humeral head sold by Biomet of Warsaw, Ind. and disclosed in U.S. patent application Ser. No. 11/357,794 and related applications, which are incorporated herein by reference.

One skilled in the art will recognize that the present teachings can be provided in various forms in addition to those illustrated. For example and with additional reference to FIGS. 6-10, the substrate 40 can be provided in a variety of different forms. Features of the substrates illustrated in FIGS. 6-10 that are generally similar to features of the substrate 40 described above are designated using like reference numbers, but also include an alphanumeric designator. While the substrates of FIGS. 6-10 are illustrated as offset substrates, one skilled in the art will recognize that they may also be provided in non-offset form.

Figure 6A:
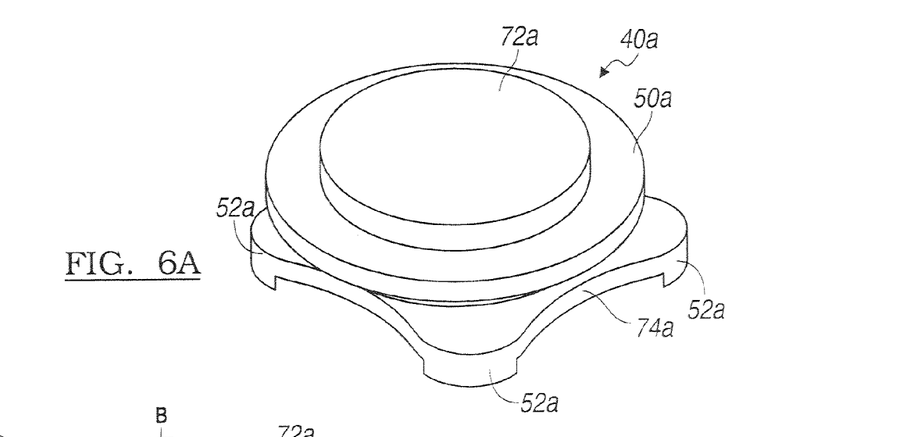
FIG. 6A is a perspective view of a head substrate according to the present teachings.
Figure 6B:
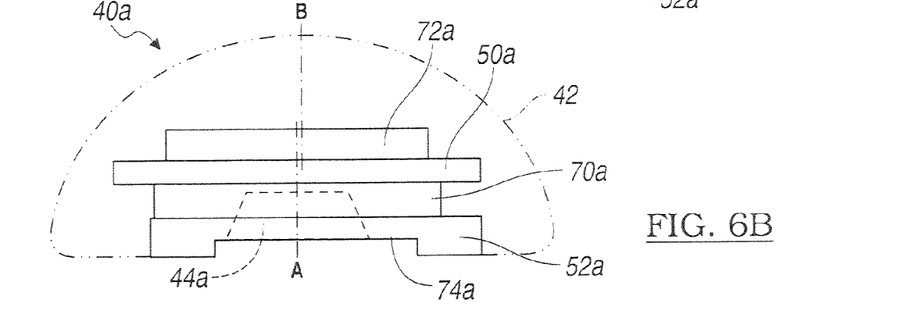
FIG. 6B is a side view of the substrate of FIG. 6A.
Figure 6C:
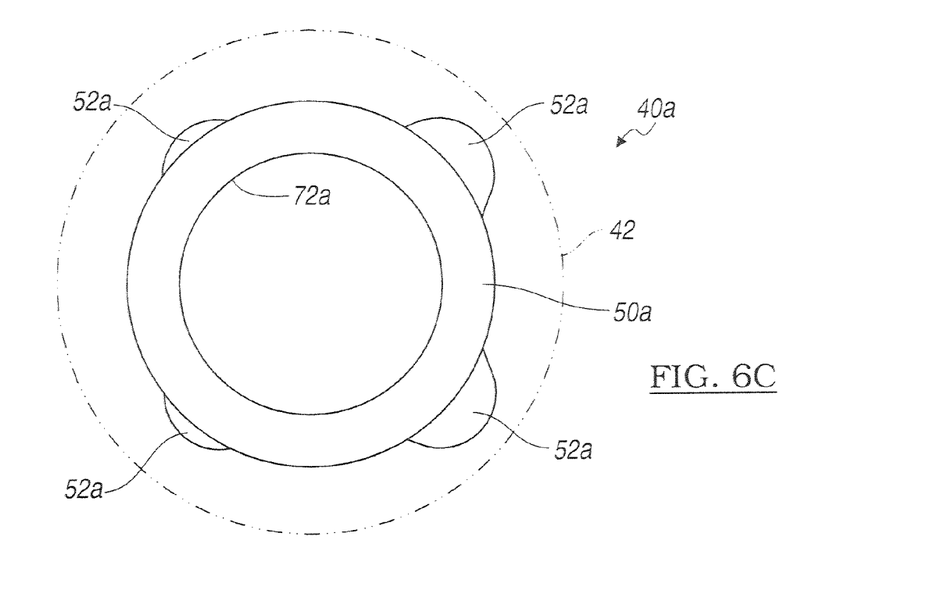
FIG. 6C is a top view of the substrate of FIG. 6A.

With initial reference to FIGS. 6A-6C, a substrate 40a is illustrated. The substrate 40a generally includes a flange 50a that is operable to secure the polymeric cover 42 to the substrate 40a. The flange 50a is between a first base portion 70a and a second base portion 72a. As illustrated, the first base portion 70a is below the flange 50a and the second base portion 72a is atop the flange 50a. Below the first base portion 70a is an anti-rotation layer 74a having a series of tabs 52a extending therefrom that are operable to prevent the polymeric cover 42 from rotating about the substrate 40a. As illustrated, the anti-rotation layer 74a has four tabs 52a. A coupling taper 44a is within the anti-rotation layer 74a and the first base portion 70a. The coupling taper 44a is sized to cooperate with the taper adaptor 16. An axis A of the coupling taper 44a is offset from an axis B of the polymeric cover 42. Further, the anti-rotation layer 74a is offset from the first and the second base portions 70a and 72a.

Figure 7A:
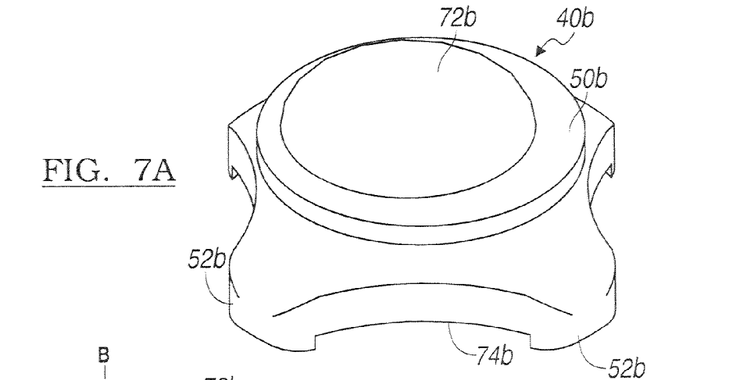
FIG. 7A is a perspective view of a head substrate according to additional aspects of the present teachings.
Figure 7B:
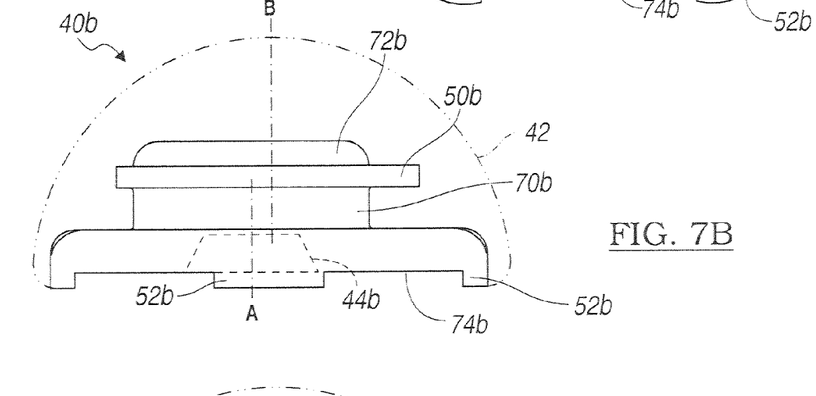
FIG. 7B is a side view of the substrate of FIG. 7A.
Figure 7C:
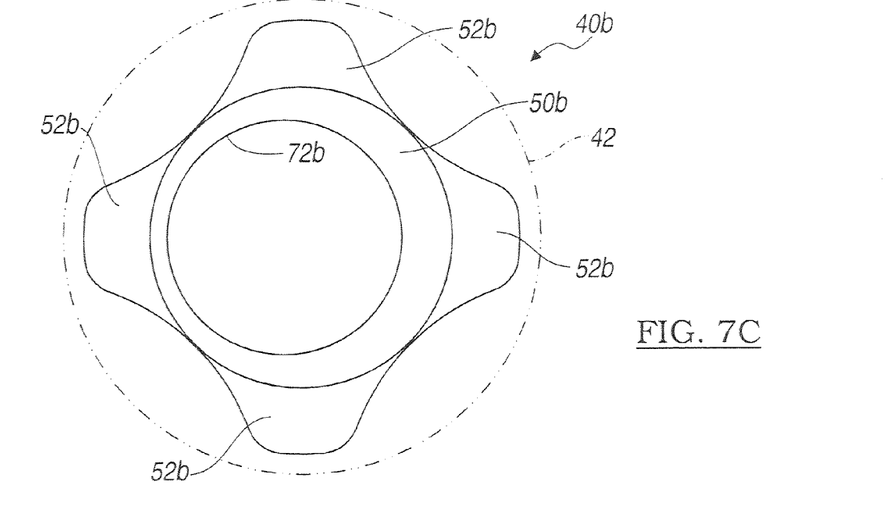
FIG. 7C is a top view of the substrate of FIG. 7A.

With reference to FIGS. 7A-7C, a substrate 40b is illustrated. The substrate 40b generally includes a flange 50b that is operable to secure the polymeric cover 42 to the substrate 40b. As illustrated, the flange 50b is atop a first base portion 70b and beneath a second base portion 72b. Below the first base portion 70b is an anti-rotation layer 74b with tabs 52b that are operable to prevent the polymeric cover 42 from rotating about the substrate 40b. A coupling taper 44b is within anti-rotation layer 74b and is sized to cooperate with the taper adaptor 16. An axis A of the coupling taper 44b and the first and the second base portions 70b and 72b is offset from an axis B of the polymeric cover 42.

Figure 8A:
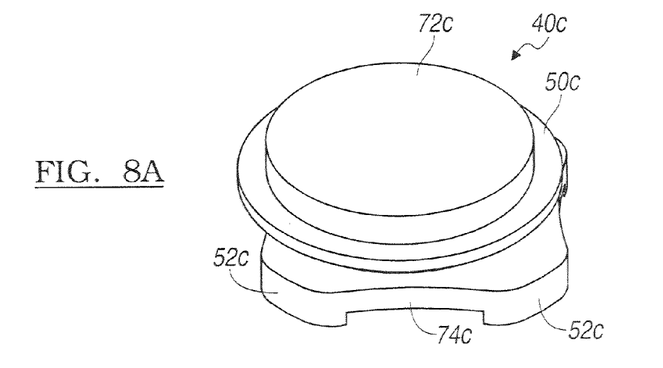
FIG. 8A is a perspective view of a head substrate according to further aspects of the present teachings.
Figure 8B:
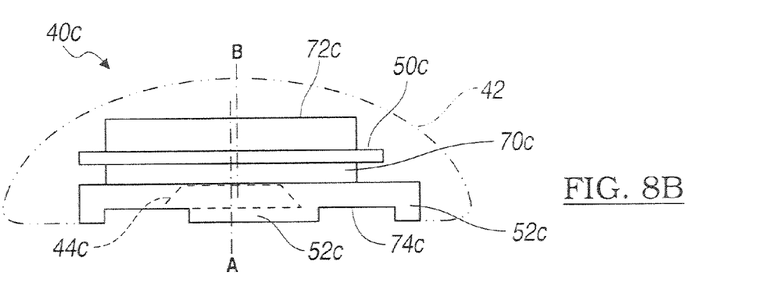
FIG. 8B is a side view of the substrate of FIG. 8A.
Figure 8C:
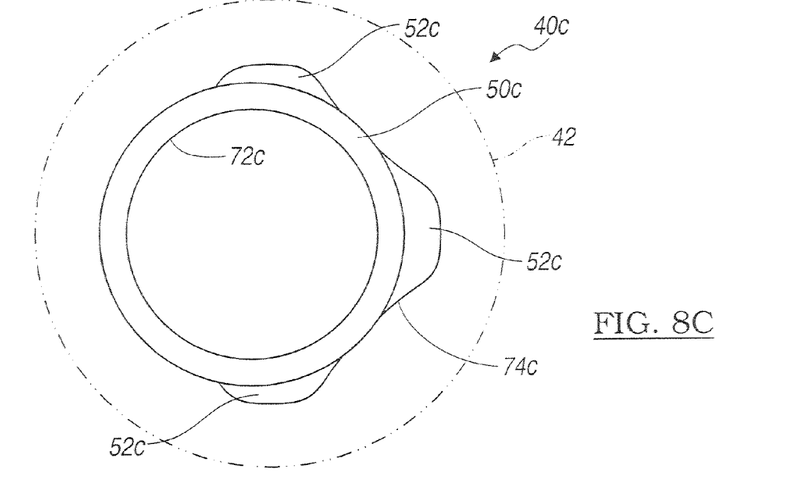
FIG. 8C is a top view of the substrate of FIG. 8A.

With reference to FIGS. 8A-8C, a substrate 40c is illustrated. The substrate 40c generally includes a flange 50c between a first base portion 70c and a second base portion 72c. Below the first base portion 70c is an anti-rotation layer 74c with tabs 52c. A coupling taper 44c is within the anti-rotation layer 74c. An axis A of the coupling taper 44c is offset from an axis B of the polymeric cover 42.

Figure 9A:
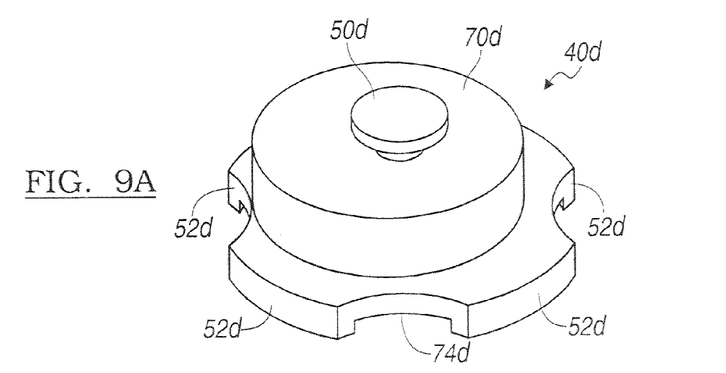
FIG. 9A is a perspective view of a head substrate according to additional aspects of the present teachings.
Figure 9B:
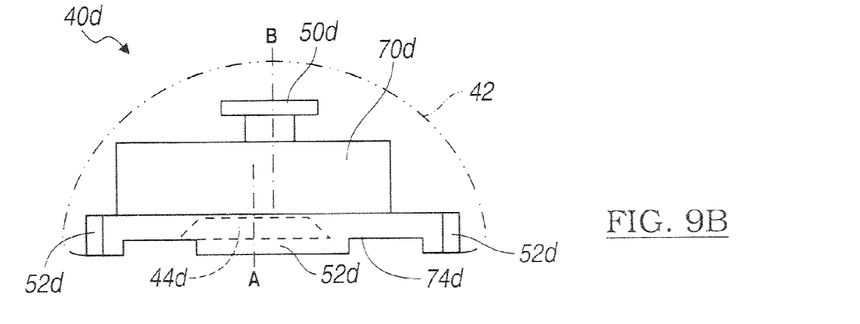
FIG. 9B is a side view of the substrate of FIG. 9A.
Figure 9C:
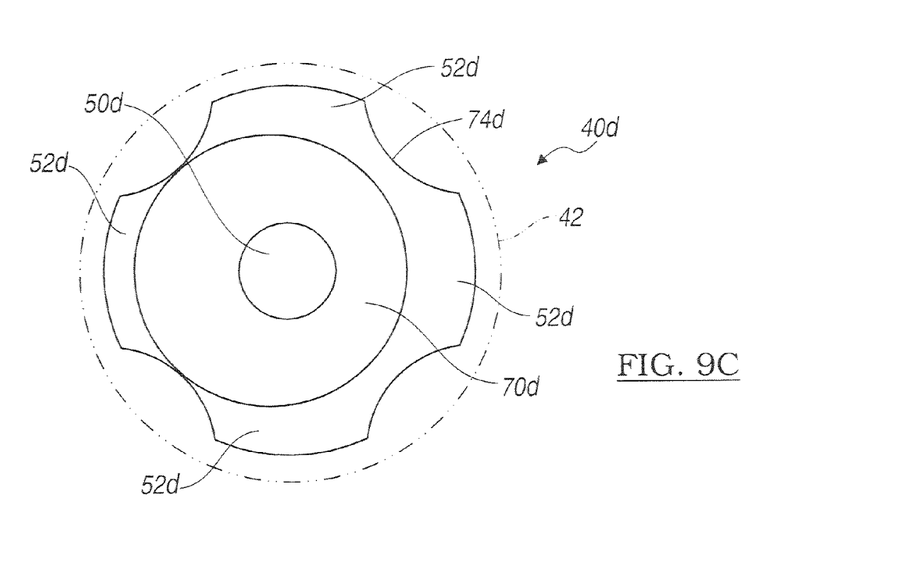
FIG. 9C is a top view of the substrate of FIG. 9A.

With reference to FIGS. 9A-9C, a substrate 40d is illustrated. The substrate 40d includes a flange 50d that sits atop a base portion 70d. The flange 50d is a retention feature that secures the polymeric cover 42 to the substrate 40d. Below the base portion 70d is an anti-rotation layer 74d. A coupling taper 44d is within the anti-rotation layer 74d. An axis A of the coupling taper 44d and the base portion 70d is offset from an axis B of the polymeric cover 42.

Figure 10A:
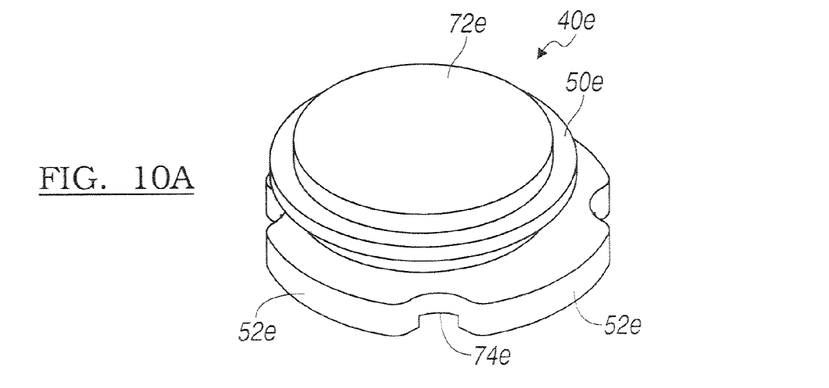
FIG. 10A is a perspective view of a head substrate according to further aspects of the present teachings.
Figure 10B:
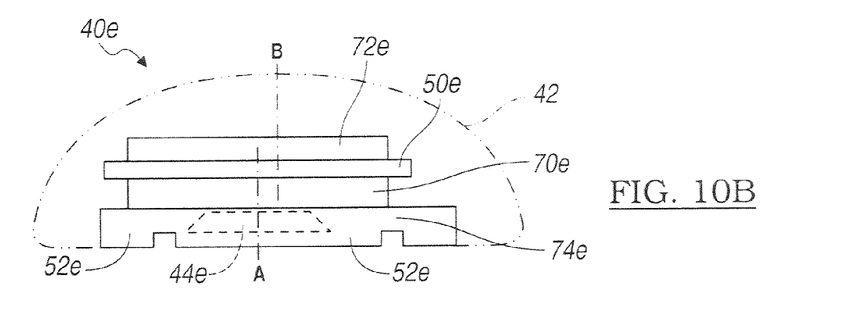
FIG. 10B is a side view of the substrate of FIG. 10A.
Figure 10C:
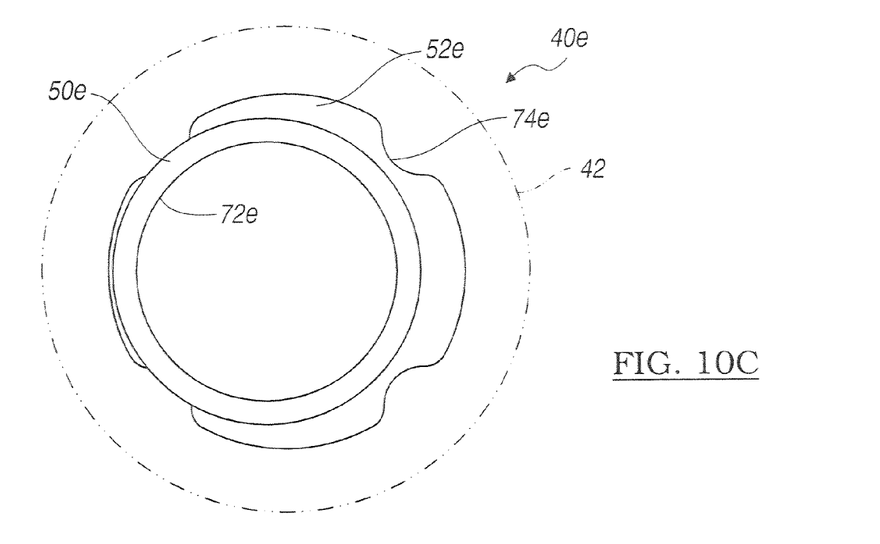
FIG. 10C is a top view of the substrate of FIG. 10A.

With reference to FIGS. 10A-10C, a substrate 40e is illustrated. The substrate 40e generally includes a flange 50e between a first base portion 70e and a second base portion 72e. Below the first base portion 70e is an anti-rotation layer 74e with tabs 52e. A coupling taper 44e is within the anti-rotation layer 74e. An axis A of the coupling taper 44e and the first and the second base portions 70e and 72e is offset from an axis B of the polymeric cover 42.

The substrates 40a-40e provide a customized head height and shape for different patients. For example, if a lower or flatter head is desirable, less polymeric material can be used over each of the different substrates 40a-40e. Further, each of the first base portions 70a-70e and/or the second base portions 72a-72e can be made thinner. Making the first base portions 70a-70e thinner positions the flanges 50a-50e closer to the respective anti-rotation layers 74a-74e.

Conversely, if a higher, or more rounded head is desirable, additional polymeric material can be used over each of the different substrates 40a-40e. Further, each of the first base portions 70a-70e and/or the second base portions 72a-72e can be made with an increased thickness. Increasing the thickness of the first base portions 70a-70e positions the flanges 50a-50e further from the respective anti-rotation layers 74a-74e. The change in position of the flanges 50a-50e can be represented as changes with respect to any fixed location of the substrates 40a-40e, such as with respect to the coupling tapers 44a-44e or any other interface surface.

With exemplary reference to FIGS. 7A-C and 8A-C, the first base portion 70b is thicker or taller than the first base portion 70c. The distance between the flange 50b and the anti-rotation layer 74b is greater than the distance between the flange 50c and the anti-rotation layer 74c. As a result, the polymeric cover 42 of the substrate 40b is more rounded and is higher than the polymeric cover 42 of the substrate 40c. Thus, the flanges 50a-50e are a first distance from the respective anti-rotation layers 74a-74e when the polymeric cover 42 has a first radius of curvature and the flanges 50a-50e are a second distance from the respective anti-rotation layers 74a-74e when the polymeric cover 42 has a second radius of curvature. Multiple heads 18 each having a different size, shape, and/or radius of curvature can be provided together in a kit.

Figure 11A:
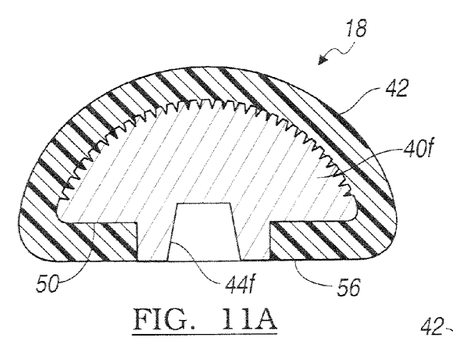
FIG. 11A is a cross-sectional view of an additional head according to the present teachings.

With additional reference to FIG. 11A, an additional substrate according to the present teachings is illustrated at reference numeral 40f. Unlike the other substrates described herein, the substrate 40f does not have a flange to retain the polymeric cover 42. Instead, the substrate 40f includes a knurled surface 76. The knurled surface 76 retains the polymeric cover 42, which is molded thereto, and helps provide the cover 42 with a uniform thickness.

Figure 12A:
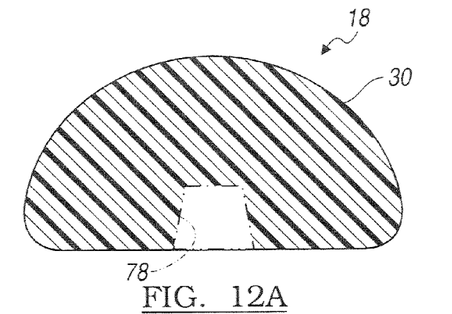
FIG. 12A is a side-view of a head according to the present teachings.

With additional reference to FIG. 12A, the head 18 can also be made entirely out of a suitable polymeric material, such as ultra-high molecular weight polyethylene, polyether ether ketone ("PEEK"), carbon fiber reinforced PEEK (such as PEEK-OPTIMA® from Invibio, Ltd. of the United Kingdom), and/or vitamin E stabilized highly crosslinked polyethylene (HXLPE) (such as E1™ Antioxidant Infused Technology by Biomet Orthopedics, Inc. of Warsaw, Ind.). A female taper 78 can be formed out of the polymeric material of the head 18, thus making the substrate 40 unnecessary. The female taper 78 can be sized and shaped to cooperate with the first male taper 36 of the taper adaptor 16 to create a Morse taper between the taper adaptor 16 and the head 18.

The female taper 78 can be provided in the polymeric head 18 in any suitable manner. For example, the convex articulating surface 30 can be formed by injection molding and the female taper 78 can subsequently be machined therein. To support the head 18 as the taper 78 is machined therein, support material can be added to the convex articulating surface 30 during the molding process. This support material can be removed after the taper 78 is complete. Alternatively, the taper 78 can be machined into a blank block of polymeric material having a boss or other support surface by which the block can be held as the taper 78 is machined therein. The block can be supported at the newly formed taper 78 and the convex articulating surface 30 can be subsequently machined therein.

Figure 11B:
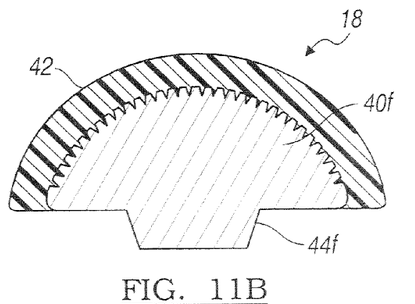
FIG. 11B is a cross-sectional view of a head according to further aspects of the present teachings.
Figure 12B:
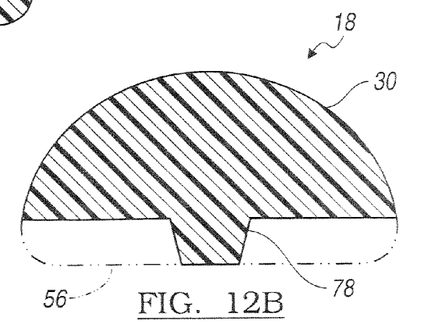
FIG. 12B is a cross-sectional view of a head according to further aspects of the present teachings.

One of ordinary skill in the art will recognize that each of the taper locks described herein can be modified such that the male and female sides of the tapers are reversed. For example, the female taper 44f illustrated in FIG. 11A can be a male taper 44f as illustrated in FIG. 11B and the taper adaptor 16 can be provided with a female taper for cooperation therewith. Further, the female taper 78 of FIG. 12A can be a male taper 78 as illustrated in FIG. 12B.

The foregoing description of the embodiments has been provided for purposes of illustration and description. It is not intended to be exhaustive or to limit the invention. Individual elements or features of a particular embodiment are generally not limited to that particular embodiment, but where applicable are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A head for a shoulder implant assembly comprising:
a polymeric cover including a convex outer surface and a generally planar base; and
a metal substrate with the polymeric cover mounted thereto, the metal substrate including:
an anti-rotation layer;
a coupling taper defined within the anti-rotation layer;
a retention flange between a first base portion and a second base portion, the retention flange configured to secure the polymeric cover to the metal substrate; and
a plurality of anti-rotation tabs extending from the anti-rotation layer configured to prevent the polymeric cover from rotating about the metal substrate;
wherein the polymeric cover covers the first base portion, the flange, and the second base portion, and is arranged between the tabs.

2. The head of claim 1, wherein the polymeric cover includes at least one of carbon fiber reinforced polyether ether ketone and vitamin E stabilized highly crosslinked polyethylene.

3. The head of claim 1, wherein a first axis extends through a center of the polymeric cover and a second axis extends through a center of the coupling taper of the metal substrate, the first axis is parallel to and spaced apart from the second axis.

4. A shoulder implant assembly comprising:
a humeral stem configured to be inserted into a humerus bone;
a head including a metal substrate and a polymeric cover mounted to the metal substrate, the metal substrate including:
a first base portion;
a second base portion;
a flange between the first base portion and the second base portion, the flange configured to secure the polymeric cover to the metal substrate;
an anti-rotation layer on a side of the first base portion opposite to the flange;

a coupling taper defined within the anti-rotation layer; and a plurality of tabs extending radially outward from the anti-rotation layer, the tabs configured to prevent the polymeric cover from rotating about the substrate;

a cup including a unitary metallic base defining a concave articulating surface that is configured to articulate with the polymeric cover of the head; and a taper adaptor including a first male taper configured to mate with the coupling taper of the head and a second male taper configured to mate with the humeral stem, the first male taper is offset from the second male taper;

wherein a first longitudinal axis extending through a center of the polymeric cover is parallel to and offset from a second longitudinal axis extending through a center of each of the coupling taper, the first base portion, and the second base portion; and wherein the polymeric cover is molded over the first base portion, the second base portion, and the flange, and is arranged between the tabs.

5. The shoulder implant assembly of claim 4, wherein the polymeric cover includes at least one of carbon fiber reinforced polyether ketone and vitamin E stabilized highly crosslinked polyethylene.

6. The shoulder implant assembly of claim 4, wherein each of the cup and the metal substrate include at least one of cobalt-chrome and titanium.

7. The shoulder implant assembly of claim 4, wherein a first axis extends through a center of the polymeric cover and a second axis extends through a center of the coupling taper, the first axis is parallel to and offset from the second axis.

8. The shoulder implant assembly of claim 4, wherein the flange is substantially circular and includes a center that is offset from the second longitudinal axis.

* * * * *